United States Patent [19]

Ayame et al.

[11] 4,415,476

[45] Nov. 15, 1983

[54] SILVER-BASED CATALYST CONTAINING CHLORINE AS AN ANIONIC COMPONENT FOR THE PRODUCTION OF ETHYLENE OXIDE

[75] Inventors: Akimi Ayame, Muroran; Naohiro Nojiri; Yukio Sakai, both of Ami, all of Japan

[73] Assignee: Mitsubishi Petrochemical Co. Ltd., Tokyo, Japan

[21] Appl. No.: 349,978

[22] Filed: Feb. 18, 1982

[30] Foreign Application Priority Data

Feb. 25, 1981 [JP] Japan ................................ 56-25417

[51] Int. Cl.³ ............................................ B01J 27/10
[52] U.S. Cl. .................................... 502/224; 549/200
[58] Field of Search ........................................ 252/441

[56] References Cited

U.S. PATENT DOCUMENTS

| | | | |
|---|---|---|---|
| 2,615,900 | 10/1952 | Sears | 252/441 X |
| 2,799,687 | 7/1957 | Gould et al. | 252/441 X |
| 3,132,157 | 5/1964 | Endler et al. | 252/441 X |
| 3,637,629 | 1/1972 | Dorfman et al. | 252/441 X |

*Primary Examiner*—Patrick Garvin
*Attorney, Agent, or Firm*—Sherman & Shalloway

[57] ABSTRACT

A catalyst comprises sodium and cesium as a cationic component and chlorine as an anionic component in addition to silver which is a typical conventional catalyst component for the production of ethylene oxide by oxidation of ethylene. Use of the catalyst of the invention gives ethylene oxide at an improved selectivity.

8 Claims, 1 Drawing Figure

SILVER-BASED CATALYST CONTAINING CHLORINE AS AN ANIONIC COMPONENT FOR THE PRODUCTION OF ETHYLENE OXIDE

BACKGROUND OF THE INVENTION

This invention relates to a process for the production of ethylene oxide by oxidizing ethylene, and to a catalyst therefor. It is based on the new discovery that a combination of sodium, cesium and chlorine with silver provides a catalyst having increased performance in the oxidation of ethylene.

A silver catalyst is substantially the sole catalyst component used in the industrial production of ethylene oxide by the oxidation of ethylene with molecular oxygen. Silver alone, however, did not prove to be a perfect industrial catalyst, and efforts have been made to increase its performance by including various additives (for example, U. S. Pat. Nos. 2238471, 2404438, 2671764 and 2799687). Many of these efforts have been directed to the addition of alkali metals (for example, British Pat. No. 1,413,251 and U.S. Pat. No. 4,212,772). Usually, halogen compounds of these metals are excluded because they are a poison to silver.

The present inventors have made extensive investigations about the effects of anionic components as well as alkali metals as cationic components. These investigations have led to the discovery that the use of chlorine previously believed to have a poisonous action, in combination with sodium and cesium unexpectedly gives a catalyst having greatly increased performance.

SUMMARY OF THE INVENTION

According to this invention, there is provided a catalyst for the production of ethylene oxide by oxidation of ethylene, comprising
 (A) silver,
 (B) (1) more than 1000 ppm (mg/kg of the catalyst) of sodium, and (2) cesium
as a cationic component, and
 (C) chlorine as an anionic component.

In another aspect, there is provided a process for producing ethylene oxide, which comprises contacting ethylene and a gas containing molecular oxygen with the aforesaid catalyst at a temperature of 180° to 300° C. and a pressure of 1 to 35 kg/cm².

DETAILED DESCRIPTION OF THE INVENTION

Figure 1:
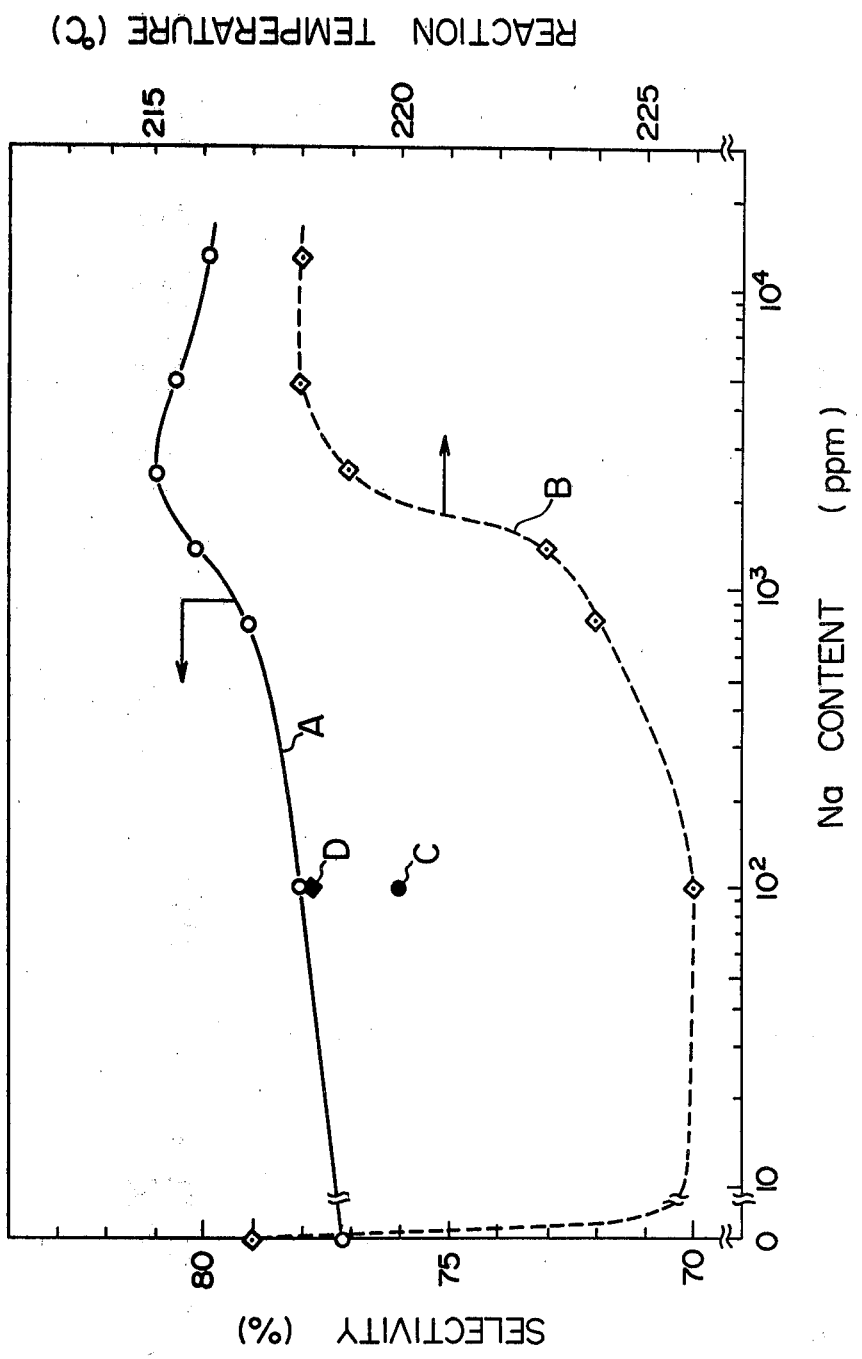
FIG. 1 is a graph showing the effect of the sodium contents of the catalysts used in Examples 7 and 10 and Comparative Examples 6 to 9 on the selectivities of the catalysts and the reaction temperatures.

In the preparation of the catalyst of this invention, a sodium compound to be added is preferably in the form of sodium carbonate, sodium bicarbonate or sodium nitrate. It may, however, be in the form of a hydroxide, nitrite, sulfate, borate, silicate, phosphate, halide or carboxylate (e.g., sodium acetate or sodium oxalate), or a mixture of any of these compounds with sodium carbonate or sodium bicarbonate.

A cesium compound to be added is preferably in the form of a chloride, bromide and/or fluoride depending upon the type of the halogen element to be added to the catalyst. It may be added in the form of any of the water-soluble or water-insoluble compounds such as its hydroxide or salts such as the nitrate, nitrate, carbonate and sulfate.

Sources of the chlorine may be sodium chloride or cesium chloride which are salts of chlorine with sodium or cesium, or other salts such as $BaCl_2$, $NH_4Cl$, $LiCl$, $KCl$ and $RbCl$.

In any case, it is essential to add sodium, cesium and chlorine as well as silver, and a combination of these gives a catalyst having greatly increased performance.

The amount of sodium added is more than 1000 ppm (mg/kg of catalyst) based on the catalyst. Preferably, it is from 1100 ppm to 1.50% by weight, more preferably 1200 ppm to 1% by weight. Advantageously, the amount of sodium added ranges from 1300 ppm to 5000 ppm. Preferably, the amount of sodium is such that the atomic ratio of Na to Ag is not more than 0.58, especially not more than 0.45. When the amount of sodium is too large, both the activity and selectivity of the catalyst are reduced. When it is too small, the dispersion of silver particles on a carrier is worse than that in the catalyst of this invention as observed by a scanning electron microscope; hence, the activity of the catalyst is low and a higher bath (reaction) temperature is required in order to obtain the same activity, with the consequence that the effect of adding halogen is not fully produced.

The suitable amount of cesium added is smaller than that of sodium. It is generally from 10 ppm to 0.5% by weight, preferably from 15 ppm to 0.1% by weight, based on the catalyst. If the amount is too large, the activity of the catalyst is markedly decreased, and if it is too small, the effect of the halogen element is not fully produced.

The suitable amount of chlorine to be added in this invention is from 5 ppm to 0.1% by weight, preferably from 7 ppm to 0.07% by weight. The addition of too large an amount results in the exhibition of its poisoning action and causes a drastic reduction in the performance of the catalyst. Thus, the characteristic feature of the invention is that chlorine previously believed to have a poisoning action has been found to have an action of a performance improver by adding it in a very small amount in combination with sodium and cesium.

In the catalyst of this invention, the cationic component is not limited to sodium and cesium, and a small amount of a third component such as lithium, barium, rubidium, potassium and thallium may be added together.

The above catalyst components are used in the form of a supported catalyst mainly from the standpoint of economy and active lifetime. A porous refractory material is used as a carrier. Desirably, the carrier has a BET surface area of 0.05 to 10 $m^2/g$ and an apparent porosity of at least 15%. A carrier composed of alpha-alumina as a main component (a so-called alundum carrier) is preferred.

Deposition of sodium, cesium and chlorine may be effected by dissolving or dispersing the aforesaid compounds of these ingredients in an aqueous solvent, impregnating a carrier with the resulting solution or dispersion, and drying the impregnated carrier under heat in the presence of a gas such as nitrogen or air. Sodium, cesium and chlorine may be deposited simultaneously or separately in any desired stage of catalyst preparation in various modes. For example, similar effects can be obtained by performing the deposition before, during or after the impregnation of the silver compound.

Deposition of silver can be carried out by dipping a carrier molded in a suitable form such as spheres, pellets or rings in an aqueous solution or dispersion prepared by dissolving or dispersing a silver compound such as silver oxalate, silver nitrate or silver lactate in water in the presence or absence of a solubilizing agent such as ethylenediamine, drying the impregnated carrier, and calcining it at a suitable temperature in a stream of a gas such as nitrogen, air or hydrogen. The kind of the gas and the temperature in the calcination are selected depending upon the kind of the silver salt, etc. The calcination temperature is usually 100° to 1000° C., preferably 150° to 700° C. The amount of silver supported in the catalyst is usually 1 to 25% by weight, preferably 3 to 20% by weight, based on the catalyst.

The silver-based catalyst of this invention is used conveniently in the production of ethylene oxide by the oxidation of ethylene in the vapor phase with molecular oxygen. The reaction conditions for the oxidation of ethylene are known, and broadly described in the prior art literature. In the production of ethylene oxide in the presence of the silver-based catalyst of this invention, the reaction pressure is 1 to 35 kg/cm$^2$, preferably 5 to 20 kg/cm$^2$; the reaction temperature is 180° to 300° C., preferably 190° to 260° C.; ethylene is used in an amount of 1 to 40% by volume, preferably 15 to 35% by volume; and oxygen is used in an amount of 1 to 20% by volume, preferably 5 to 10% by volume, diluted with a diluting agent such as methane and nitrogen, preferably methane, in an amount of 20 to 70% by volume, preferably 30 to 65% by volume. Oxygen may be supplied in the form of air or industrial oxygen. Preferably, a reaction inhibitor such as a halogenated hydrocarbon is added to the starting gaseous mixture. In particular, by adding several ppm to several ten ppm (by weight) of ethylene dichloride, vinyl chloride, etc. to the starting gas, the formation of hot spots in the catalyst can be prevented and the properties, especially the selectivity, of the catalyst can be greatly improved. The starting gaseous mixture is continuously introduced into a reactor filled with the catalyst. The resulting ethylene oxide is separated and recovered from the reaction mixture by using customary methods.

The following examples illustrate the present invention more specifically.

EXAMPLE 1

AgNO$_3$ (6.0 g) was dissolved in 100 ml of water, and separately, 3.4 g of potassium oxalate (K$_2$C$_2$O$_4$.H$_2$O) was dissolved in water. The resulting solutions were mixed, and heated in a water bath to 60° C. to form a white precipitate of silver oxalate. Centrifugation and washing with distilled water were repeated to remove potassium from the precipitate.

Separately, 6.6 ml of 1:1 mixture of ethylenediamine and water was prepared, and while cooling with ice, the silver oxalate precipitate was gradually dissolved in the mixture to prepare a silver solution. Thirty grams of an alpha-alumina carrier (SA-5161, a tradename for a product of Norton Company) was dipped in the silver solution, and after allowing the excess of the solution to flow out, was dried at 80° C. under reduced pressure in a rotary evaporator. The dried carrier was transferred into a calcination tube. The temperature was raised to 300° C. in a stream of nitrogen over the course of 2 hours, and it was further calcined at this temperature for 2 hours to deposit silver on the carrier.

Then, 2.0 g of Na$_2$CO$_3$ and 0.04 g of CsCl were dissolved in 50 ml of a mixture of methanol and water (methanol content 30% by weight), and the silver-supported carrier was dipped in it. The excess of the solution was removed by filtration, and the impregnated carrier was dried at 110° C. for 2 hours in a stream of nitrogen gas to prepare a catalyst in accordance with this invention. The proportion of Ag supported was 8.0% by weight, and the proportions of Na, Cs and Cl supported were 0.35% by weight, 126 ppm, and 34 ppm, respectively.

The catalyst was pulverized to a size of 9 to 28 mesh, and 10 g of the pulverized catalyst was filled in a steel reactor having an inside diameter of 20 mm. A gaseous mixture consisting of 30% by volume of ethylene, 8% by volume of oxygen, 2 ppm of vinyl chloride and the balance being methane was passed through the reactor at a pressure of 9 kg/cm$^2$ and an SV of 2000 hr$^{-1}$. At a bath temperature (reaction temperature) of 200° C., an oxygen conversion of 35% and an ethylene oxide selectivity of 81.0% were obtained. At 207° C., the oxygen conversion was 61.0% and the ethylene oxide selectivity was 75%. During the three-week continuous operation, no change was noted in the performance of the catalyst.

EXAMPLE 2

Thirty grams of an alpha-alumina carrier (SA-5161) was dipped in 50 ml of an aqueous solution containing 2.0 g of sodium carbonate. Excess solution was removed by filtration, and the impregnated carrier was dried at 110° C. for 2 hours in a stream of nitrogen gas to prepare a carrier impregnated with sodium carbonate.

Silver was deposited on the carrier in the same way as in Example 1. The carrier was then dipped in a solution of 0.02 g of cesium chloride in 50 ml of a mixture of methanol and water (water content 0.3% by weight). The excess of the solution was removed, and the impregnated carrier was dried at 110° C. for 2 hours in a stream of nitrogen gas to prepare a catalyst in accordance with this invention. The proportion of Ag deposited was 8.0% by weight, and the proportions of Na, Cs and Cl deposited were 0.35% by weight, 63 ppm and 17 ppm, respectively.

Ethylene was oxidized under the same conditions as in Example 1 using the resulting catalyst. At a reaction temperature of 195° C., an oxygen conversion of 32% and an ethylene oxide selectivity of 80.0% were obtained.

COMPARATIVE EXAMPLE 1

The procedure of Example 1 was followed except that the amount of sodium carbonate was decreased to one-tenth, and the amount of cesium chloride added was decreased to one-half. Thus, there was prepared a supported catalyst containing 8.0% by weight of Ag, 350 ppm of Na, 63 ppm of Cs and 17 ppm of Cl. Ethylene was oxidized under the same conditions as in Example 1 using the resulting catalyst. At a reaction temperature of 195° C., an oxygen conversion of 23% and an ethylene oxide selectivity of 79.5% were obtained.

EXAMPLE 3

Silver was deposited on a carrier (SA-5161) in the same way as in Example 1.

The silver-supported carrier was then dipped in a solution of 2.0 g of sodium carbonate, 0.13 g of cesium nitrate and 0.014 g of sodium chloride in 50 ml of a mixture of methanol and water (methanol content 30% by weight). The excess solution was removed, and the impregnated carrier was dried at 110° C. for 2 hours in a stream of nitrogen gas to prepare a catalyst in accordance with this invention.

The proportion of Ag deposited was 8% by weight, and the proportions of Na, Cs and Cl deposited were 0.35% by weight, 315 ppm, and 34 ppm, respectively.

COMPARATIVE EXAMPLES 2 to 5

Four different catalysts having the compositions shown in Table 1 were prepared in the same way as in Example 1, and tested under the same reaction conditions as in Example 1. The results together with those obtained in Example 1 are summarized in Table 1. It is seen from Table 1 that the catalyst of this invention shows higher selectivity.

TABLE 1

| Run | | Composition of the catalyst | Raw materials added | Reaction temperature (°C.) | Oxygen conversion (%) | Selectivity (%) |
|---|---|---|---|---|---|---|
| Example | 1 | Ag—Na—Cs—Cl<br>8  0.35  126  34<br>wt % wt % ppm ppm | $Na_2CO_3$, CsCl | 207 | 61.0 | 75 |
| Comparative Example | 2 | Ag—Na<br>8  0.35<br>wt % wt % | $Na_2CO_3$ | 205 | 60.2 | 70.3 |
| | 3 | Ag—Cs—Cl<br>8  126  34<br>wt % ppm ppm | CsCl | 228 | 60.0 | 68.0 |
| | 4 | Ag—Na—Cs<br>8  0.35  126<br>wt % wt % ppm | $Na_2CO_3$, $CsNO_3$ | 200 | 58.5 | 67.7 |
| | 5 | Ag  Na  Cl<br>8  0.35  34<br>wt % wt % ppm | $Na_2CO_3$, NaCl | 206 | 68.0 | 66.5 |

Ethylene was oxidized under the same conditions as in Example 1 using the resulting catalyst. At a reaction temperature of 210° C., an oxygen conversion of 34.5% and an ethylene oxide selectivity of 80.0% were obtained.

EXAMPLE 4

A supported catalyst containing 8.0% by weight of Ag, 0.22% by weight of Na, 126 ppm of Cs and 34 ppm of Cl was prepared in the same way as in Example 1 except that 2.0 g of sodium bicarbonate was used instead of sodium carbonate. Ethylene was oxidized under the same conditions as in Example 1 using the resulting catalyst. At a reaction temperature of 215° C., an oxygen conversion of 30.0% and an ethylene oxide selectivity of 81.0% were obtained.

EXAMPLE 5

A supported catalyst containing 8.0% by weight of Ag, 0.23% by weight of Na, 126 ppm of Cs and 34 ppm of Cl was prepared in the same way as in Example 1 except that 2.0 g of sodium acetate was used instead of sodium carbonate. Ethylene was oxidized under the same conditions as in Example 1 using the resulting catalyst. At a reaction temperature of 218° C., an oxygen conversion of 30.0% and an ethylene oxide selectivity of 81.0% were obtained.

EXAMPLE 6

A supported catalyst containing 8.0% by weight of Ag, 0.24% by weight of Na, 126 ppm of Cs and 34 ppm of Cl was prepared in the same way as in Example 1 except that 2.0 g of sodium nitrate was used instead of sodium carbonate. Ethylene was oxidized under the same reaction conditions as in Example 1 using the resulting catalyst. At a reaction temperature of 219° C., an oxygen conversion of 34.0% and an ethylene oxide selectivity of 80.5% were obtained.

EXAMPLE 7

Thirty grams of an alpha-alumina carrier (SA-5161) was dipped in 50 ml of an aqueous solution containing 2.2 g of sodium bicarbonate. The excess solution was removed by filtration, and the impregnated carrier was dried at 110° C. for 2 hours in a stream of nitrogen gas to prepare a sodium bicarbonate-impregnated carrier.

Silver nitrate (6.0 g) was dissolved in 100 ml of water, and 3.4 g of potassium oxalate ($K_2C_2O_4.H_2O$) was dissolved in 100 ml of water. The aqueous solutions were mixed, and heated to 60° C. in a water bath to form a white precipitate of silver oxalate. Centrifugation and washing with distilled water were repeated to remove potassium from the precipitate.

Separately, 6.6 ml of a 1:1 mixture of ethylenediamine and water was prepared, and while cooling with ice, the precipitate of silver oxalate was gradually dissolved in the mixture to prepare a silver solution. The above carrier impregnated with sodium bicarbonate was dipped in the resulting silver solution. The excess of the solution was allowed to flow out, and the carrier was dried at 80° C. under reduced pressure in a rotary evaporator. The dried carrier was transferred to a calcination tube and the temperature was raised to 300° C. over the course of 2 hours. It was further calcined at this temperature for 1.5 hours. The calcined product was cooled, and dipped in 50 ml of a methanol/water mixture (water content 0.3% by weight) containing 0.043 g of cesium chloride. The excess of the solution was removed by filtration, and the impregnated carrier was dried at 110° C. for 2 hours in a stream of nitrogen to prepare a catalyst in accordance with this invention which had the composition shown in Table 2.

The catalyst was tested under the same reaction conditions as in Example 1. The results are shown in Table 2.

Examples 8 to 10

In each run, a catalyst was prepared in the same were as in Example 7 except that the content of Na was changed as shown in Table 2. The resulting catalyst was tested in the same way as in Example 7. The results are shown in Table 2.

COMPARATIVE EXAMPLES 6 to 8

In each run, a catalyst was prepared in the same way as in Example 7 except that the content of Na was outside the scope of the invention as shown in Table 2. The resulting catalyst was tested in the same way as in Example 7. The results are shown in Table 2. It is seen from Table 2 that the catalysts having an Na content outside the scope of the invention showed inferior selectivity to the catalyst of this invention.

COMPARATIVE EXAMPLE 9

A catalyst containing Cs and Na as cationic components in the same proportions as in Experiment 5C of Japanese Laid-open Patent Publication No. 127144/1980 and chlorine as an ionic component was repeated by the same catalyst preparing method using the same raw materials as in Example 7. The catalyst was tested under the same reaction conditions as in Example 7. The results are shown in Table 2. It is seen that the catalyst was inferior in selectivity to the catalyst of this invention.

TABLE 2

|  |  | Composition of the catalyst | | | | Results of the reaction | | |
| --- | --- | --- | --- | --- | --- | --- | --- | --- |
|  |  | Ag (wt %) | Na (ppm) | Cs (ppm) | Cl (ppm) | Temperature (°C.) | Oxygen conversion (%) | Selectivity (%) |
| Example | 7 | 8.4 | 2500 | 160 | 42 | 219 | 40 | 80.8 |
|  | 8 | 8.4 | 1380 | 160 | 42 | 223 | 40 | 80.2 |
|  | 9 | 8.9 | 5000 | 150 | 40 | 218 | 40 | 80.5 |
|  | 10 | 8.4 | 13000 | 160 | 42 | 218 | 40 | 79.8 |
| Comparative | 6 | 8.3 | 0 | 160 | 42 | 217 | 40 | 77.2 |
| Example | 7 | 8.4 | 100 | 160 | 42 | 226 | 40 | 78.1 |
|  | 8 | 8.4 | 800 | 160 | 42 | 224 | 40 | 78.9 |
|  | 9 | 8.4 | 100 | 50 | 13 | 218 | 40 | 76.0 |

The effect of the Na contents of the catalysts shown in Table 2 on the selectivity and reaction temperature plotted on a graph shown in FIG. 1, in which the abscissa represents the Na content (ppm) on a logarithmic scale and the axes of ordinates, the left and right ones, represent the selectivity (%) for ethylene oxide and the reaction temperature (°C.), respectively. In FIG. 1, the curve A represents the selectivity; curve B, the reaction temperature corresponding to curve A; and black points C and D, the selectivity obtained under the conditions of Comparative Example 9 and the reaction temperature employed.

It is seen from the results shown by curves A and B of FIG. 1 that when the amount of sodium added exceeds 1000 ppm, especially about 1100 ppm, based on the catalyst, the catalyst of this invention gives a markedly increased selectivity for ethylene oxide at relatively low reaction temperatures. It is also seen from FIG. 1 that when the amount of sodium added is within the range of 1200 ppm to 1% by weight, ethylene oxide can be produced at a high selectivity at low temperatures, and therefore amounts of sodium within this range are preferred.

What we claim is:

1. A catalyst for the production of ethylene oxide by oxidation of ethylene, said catalyst comprising
   (A) silver,
   (B) (1) sodium in an amount of more than 1000 ppm (mg/kg of catalyst) based on the catalyst and (2) cesium as a cationic component, the amount of cesium being smaller than that of sodium and ranging from 10 ppm to 0.5% by weight based on the catalyst, and
   (C) chlorine as an anionic component the amount of chlorine being from 5 ppm to 0.1% by weight based on the catalyst.

2. The catalyst of claim 1 wherein the amount of sodium is in the range of from 1100 ppm to 1.50% by weight based on the catalyst.

3. The catalyst of claim 1 wherein the amount of sodium is in the range of from 1200 ppm to 1% by weight based on the catalyst.

4. The catalyst of claim 1, 2 or 3 wherein the amount of cesium is in the range of from 15 ppm to 0.1% by weight based on the catalyst.

5. The catalyst of claim 1, 2 or 3 wherein the amount of chlorine is in the range of from 7 ppm to 0.07% by weight based on the catalyst.

6. The catalyst of claim 1, 2 or 3 wherein silver, sodium, cesium and chlorine as catalyst ingredients are supported on a porous refractory carrier having a surface area of 0.05 to 10 m$^2$/g and an apparent porosity of at least 15%.

7. The catalyst of claim 1, 2 or 3 wherein the atomic ratio of sodium to silver is not more than 0.58.

8. The catalyst of claim 1, 2 or 3 wherein the amount of silver in the catalyst is from 1 to 25% by weight, based in the catalyst.

* * * * *